(12) United States Patent
Von Schuckmann

(10) Patent No.: US 10,722,664 B2
(45) Date of Patent: Jul. 28, 2020

(54) MANUALLY ACTUATABLE INHALER

(71) Applicant: Alfred Von Schuckmann, Kevelaer (DE)

(72) Inventor: Alfred Von Schuckmann, Kevelaer (DE)

( * ) Notice: Subject to any disclaimer, the term of this patent is extended or adjusted under 35 U.S.C. 154(b) by 214 days.

(21) Appl. No.: 15/774,056

(22) PCT Filed: Nov. 2, 2016

(86) PCT No.: PCT/EP2016/076326
§ 371 (c)(1),
(2) Date: May 7, 2018

(87) PCT Pub. No.: WO2017/080871
PCT Pub. Date: May 18, 2017

(65) Prior Publication Data
US 2018/0326166 A1    Nov. 15, 2018

(30) Foreign Application Priority Data

Nov. 13, 2015    (DE) ........................ 10 2015 119 617

(51) Int. Cl.
*A61M 15/00*    (2006.01)
*A61M 16/14*    (2006.01)
(Continued)

(52) U.S. Cl.
CPC .... *A61M 15/0008* (2014.02); *A61M 15/0025* (2014.02); *A61M 15/0065* (2013.01);
(Continued)

(58) Field of Classification Search
None
See application file for complete search history.

(56) References Cited

U.S. PATENT DOCUMENTS 5,263,475 A    11/1993    Altermatt et al.
5,331,953 A     7/1994    Andersson et al.
(Continued)

FOREIGN PATENT DOCUMENTS

DE    690 02 353 T2    12/1993
DE    199 63 946 A1     3/2001
(Continued)

OTHER PUBLICATIONS

International Search Report of PCT/EP2016/076326, dated May 15, 2017.

*Primary Examiner* — Samchuan C Yao
*Assistant Examiner* — Savannah L Gabriel
(74) *Attorney, Agent, or Firm* — Collard & Roe, P.C.

(57) ABSTRACT

A hand operable inhalator for dispensing a powdery substance, in particular a pharmaceutical substance, with a supply chamber, a discharge channel and a dosing chamber, wherein the discharge channel protrudes into the supply chamber, and the dosing chamber and discharge channel can be moved relative to each other. In order to indicate an inhalator for dispensing a powdery substance that makes the dosing chamber advantageously fillable, the discharge channel can be rotated around a rotational axis, and that the dosing chamber can be filled while the discharge channel rotates. The inhalator can have a dosing chamber that can be moved from a closed into an open state and vice versa. The inhalator can have a discharge channel that incorporates a turbulence means, which has a helically running wall and is to carry a flow while discharging air provided with the substance.

11 Claims, 9 Drawing Sheets

(51) Int. Cl.
 *B65D 83/54* (2006.01)
 *B65D 83/48* (2006.01)
(52) U.S. Cl.
 CPC ....... *A61M 16/14* (2013.01); *A61M 2202/064* (2013.01); *A61M 2205/071* (2013.01); *A61M 2206/16* (2013.01); *B65D 83/48* (2013.01); *B65D 83/54* (2013.01)

(56) References Cited

U.S. PATENT DOCUMENTS

| | | | |
|---|---|---|---|
| 7,611,078 B2 * | 11/2009 | Zaima | A61M 15/0066 128/203.12 |
| 8,210,170 B2 | 7/2012 | Von Schuckmann | |
| 2004/0237276 A1 | 12/2004 | Zaima et al. | |
| 2007/0289593 A1 | 12/2007 | Von Schuckmann | |
| 2008/0142009 A1 | 6/2008 | Carrico et al. | |
| 2009/0260626 A1 | 10/2009 | Von Schuckmann | |

FOREIGN PATENT DOCUMENTS

| | | |
|---|---|---|
| DE | 10 2005 046 644 B3 | 7/2006 |
| DE | 10 2005 033 397 A1 | 1/2007 |
| EP | 1 905 470 A2 | 4/2008 |
| JP | H11-33116 A | 2/1999 |
| WO | 93/21980 A1 | 11/1993 |
| WO | 2006/021546 A1 | 3/2006 |

\* cited by examiner

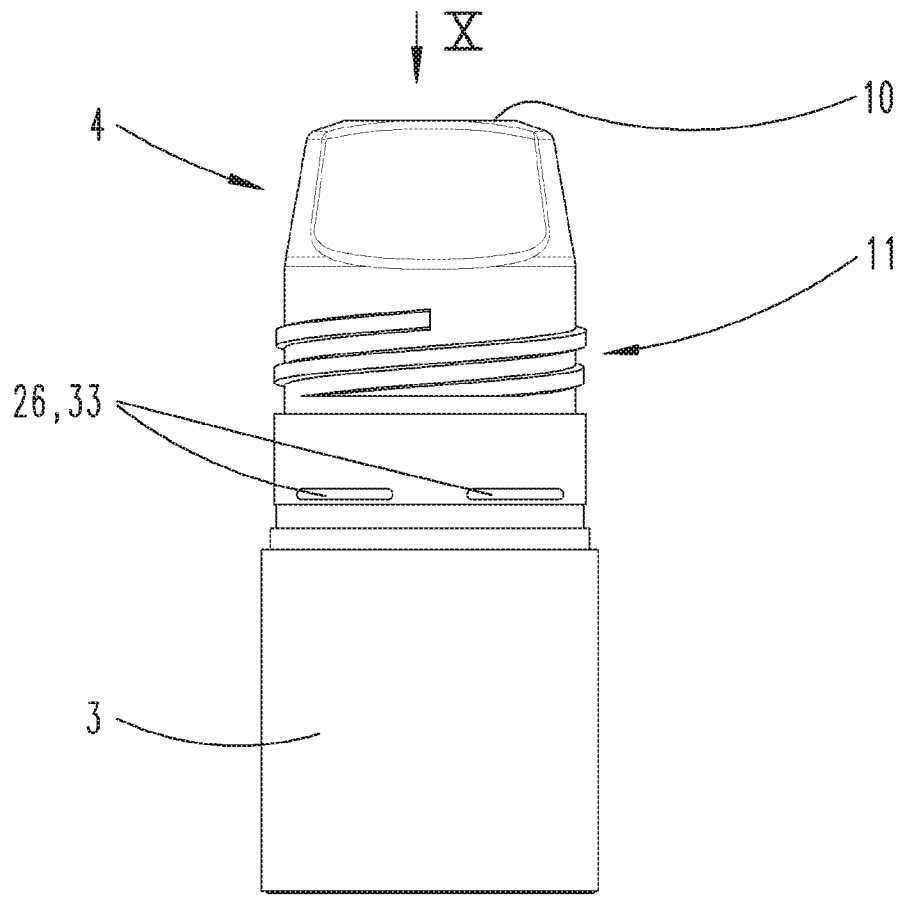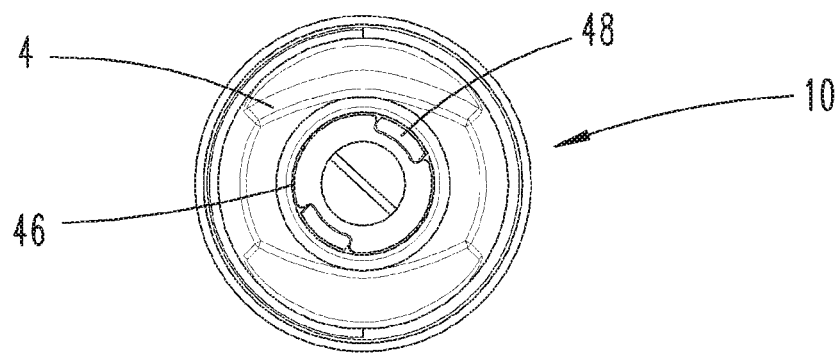

MANUALLY ACTUATABLE INHALER

CROSS REFERENCE TO RELATED APPLICATIONS

This application is the National Stage of PCT/EP2016/076326 filed on Nov. 2, 2016, which claims priority under 35 U.S.C. § 119 of German Application No. 10 2015 119 617.4 filed on Nov. 13, 2015, the disclosures of which are incorporated by reference. The international application under PCT article 21(2) was not published in English.

AREA OF TECHNOLOGY

The invention relates to a hand operable inhalator for dispensing a powdery substance, in particular a pharmaceutical substance, with a supply chamber, a discharge channel and a dosing chamber, wherein the discharge channel protrudes into the supply chamber, and the dosing chamber and discharge channel can be moved relative to each other.

In addition, the invention also relates to a hand operable inhalator in which the dosing chamber can be moved from a closed into an open state and vice versa.

The invention also relates to a hand operable inhalator in which the discharge channel incorporates a turbulence means, which has a helically running wall and is to carry a flow while discharging air provided with the substance, and the wall divides the air flowing through into first partial flows guided thereafter in an entry area given in a direction of flow.

Furthermore, the invention relates to a hand operable inhalator, in which it is important that a mouthpiece have an orifice plane, and that a closing cap for flashing the mouthpiece along with an end of the discharge channel allocated to the mouthpiece be provided.

PRIOR ART

Such inhalators are already known in various regards. Reference is initially made to WO 2006/021546 A1 (see also US 2007/0289593 A1). This known inhalator has a slider part with an opening, wherein the opening comprises the dosing chamber. The slider part can be moved between a position immersed in the supply chamber and a position pulled out of the supply chamber. In the position pulled out of the supply chamber, the dosing chamber is located in the discharge channel, which is immovable, and can be evacuated by a suction air flow of a user.

Reference is further to be made to DE 199 63 946 A1 (a modified configuration hereto was also disclosed by U.S. Pat. No. 8,210,170 B2), in which the discharge channel extends into the supply chamber, and can be moved axially between a dispensing position and filling position relative to this dosing chamber in a longitudinal direction of the inhalator. WO 93/21980A shows an inhalator, in which the dosing chamber is arranged in a rotary plate, and can be rotated so as to be displaced from a position allocated to the supply chamber into a position allocated to the fixed discharge channel.

SUMMARY OF THE INVENTION

Proceeding from the last indicated prior art, the object of the invention in one of the embodiments is to indicate an inhalator for dispensing a powdery substance, in which an advantageous fillability of the dosing chamber is achieved.

Regarding another embodiment, the invention deals with the object of achieving a favorable turbulence in the discharge channel.

Regarding yet another embodiment of the invention, the object is to favorably influence the discharge channel by means of the closing cap.

With respect to these objects, a first instruction of the invention provides as a solution for the subject matter of claim 1 that the discharge channel be rotatable around a rotational axis, and that the dosing chamber can be filled while the discharge channel rotates. The rotatability of the discharge channel allows for different embodiments with respect to filling the dosing chamber. The dosing chamber can be released for filling by the rotation, for example so that substance from the dosing chamber can enter into the released dosing chamber. However, the dosing chamber can also be forcibly filled by rotating the discharge channel by means located thereon. A combination of measures is also possible.

With respect to these objects, claim 2 provides a solution in which the supply chamber together with the discharge channel can be moved relative to the mouthpiece so as do displace the dosing chamber from a closed into an open state and vice versa.

With respect to the other object regarding the turbulence, claim 3 provides a solution in which the first partial flows ensuing in the direction of flow in an interruption area are divided into second partial flows that are thereafter also adjacently guided, wherein a second partial flow is based on a convergence of portions of both first partial flows.

Regarding the interaction between the mouthpiece and discharge channel, the solution is geared toward being able to move the discharge channel relative to the mouthpiece from a first position in which the end of the discharge channel is closer to the orifice plane, into a second position in which the end of the discharge channel is further away from the orifice plane, and vice versa, and toward providing an influencing section on the closing cap so as to at any rate cause the discharge channel to move from the first into the second position.

Additional features of the invention are often described or illustrated below, including in the description of figures and the drawing, in their preferred allocation to one, several or all concepts already explained above, but can also be important as allocated to just one or several features that were described or graphically illustrated, in particular to include those in the already discussed independent claims, or independently or in some other overall concept.

In particular, as not least also evident from the described exemplary embodiment, the features summarized in various independent claims can be realized in a combination of two, several or all of the independent claims.

The hand operable inhalator as such is preferably elongated and essentially cylindrical in design. Essential components that are provided for conventional use from an upper to a lower end can initially be an upper closing cap, and further a mouthpiece that can lie exposed after removing the closing cap. Beyond that the mentioned discharge channel, although the latter can in principle already comprise the mouthpiece. The supply chamber with discharge channel protruding therein can then follow, and allocated to the supply chamber the dosing chamber, which can respectively be filled with substance from the supply chamber.

In particular, it is further possible to also provide a reservoir for dehumidifying means and/or turbulence means involving the exiting air flow loaded with substance and/or one or several guide channels for air siphoned or introduced from outside and/or a counter.

Because the discharge channel can be rotated around a rotational axis and the dosing chamber can be filled while rotating the discharge channel, the filling of the dosing chamber is linked to the rotation of the discharge channel. From a specific standpoint, rotating the discharge channel to a substantial extent causes the dosing chamber to be filled. Since rotating the discharge channel protruding into the supply chamber is also associated with influencing the substance in the supply chamber, this influencing of the substance in the supply chamber and filling of the dosing chamber are achieved simultaneously.

With regard to the embodiment in which the supply chamber together with the discharge channel can be moved relative to the mouthpiece, a movability of the unit comprised of the discharge channel and supply chamber is achieved. For example, it can be used for favorably opening and closing the dosing chamber.

With respect to the turbulence, the division into first partial flows and convergence into second partial flows enables yet another more favorable disaggregation of the pharmaceutical portion of the substance to be ultimately inhaled. Collisions take place between parts of the powdery substance itself. The detachment of an active substance from the carrier material can advantageously be achieved.

With respect to influencing the discharge channel via the closing cap, the discharge channel can favorably be made to move by applying or removing the closing cap. In particular in an attaching or unscrewing direction of the closing cap onto the mouthpiece. If the discharge channel has been moved closer to the orifice plane in the course of using the inhalator, the closing cap can be applied to reliably ensure that the discharge channel is returned to a corresponding initial position.

In another embodiment, it is preferred that the rotational axis of the discharge channel at least partially coincide with a transport direction of substance transported through the discharge channel. The rotational axis is preferably also essentially a geometric central longitudinal axis of the preferably essentially cylindrical inhalator as a whole and/or a geometric central longitudinal axis of part of the discharge channel.

It is further preferred that the dosing chamber be eccentrically arranged to the rotational axis of the discharge channel. In this way, the dosing chamber can be filled as mentioned, but also evacuated, in particular released for evacuation by rotating the discharge channel, in a structurally still favorable manner.

The discharge channel preferably penetrates through the dosing chamber in such a way that in any event at least part of its length penetrating through the dosing chamber can be surrounded by the substance over its entire periphery transverse to a penetrating direction. This ensures that the substance is inevitably influenced by the rotating discharge channel—guided, as it were. This is also advantageous in particular in conjunction with the mentioned eccentric arrangement of the rotational axis.

The dosing chamber is further preferably designed separately from the discharge channel. The dosing chamber can here be a partial area of the supply chamber that is directly accessible from whatever other area of the supply chamber, but is formed outside of the space occupied by the rotating discharge channel overall given a complete rotation. Because the dosing chamber is separately designed from the discharge channel, no filling into the discharge channel is provided. On the other hand, the dosing chamber in the dispensing position can be situated spatially right after the discharge channel and an opening that leads to it, which then carries a flow while discharging removed substance.

In particular, it is also preferred that the dosing chamber be arranged on the floor side of the supply chamber. During conventional use, gravity alone allows substance to get into the dosing chamber for refilling purposes given a release of the dosing chamber. However, this also preferably means that the discharge channel extends through the entire supply chamber. This extension is viewed in relation to an alignment of the inhalator with the mouthpiece above and the floor of the supply chamber below, so that viewed in this way, the discharge channel penetrates through the supply chamber completely or nearly completely in a vertical direction.

The discharge channel can have a foot, which as the discharge channel rotates releases the dosing chamber for filling purposes. In the same way, this foot can also cover the dosing chamber as rotation continues. In the discussed view in the vertical direction, the foot in particular can protrude in the vertical direction above the area of the discharge channel extending above the foot relative to the rotational axis or a longitudinal extension of the discharge channel radially over the latter. The foot can simultaneously also form a flow chamber, through which substance exiting the dosing chamber with the latter covered can be guided into the adjoining area of the discharge channel.

A lower side of the discharge channel potentially formed by the discussed foot is preferably designed in-plane with a floor of the supply chamber running outside of the dosing chamber. As a consequence, the lower side of the discharge channel can run over the floor of the dosing chamber as the discharge channel rotates. In this regard, the dosing chamber is preferably formed below the floor or extending downwardly from the floor of the dosing chamber. When the lower side of the discharge channel is located above the dosing chamber, virtually closing the latter, it correspondingly yields a kind of cover. However, this is not necessarily a cover in the usual sense, since the mentioned flow path for discharge purposes can already form herein, and resultantly be present. Running over the filled dosing chamber with the foot or lower side of the discharge channel can also counter an overfilling of the dosing chamber. An advantageously uniform filling can be achieved.

In particular, the discharge channel preferably has an angled progression relative to an extension into the discharge chamber. In terms of the addressed view with the inhalator aligned with a mouthpiece at the top and the floor of the dosing chamber at the bottom, the extension into the supply chamber penetrates through the dosing chamber essentially from the top down, i.e., vertically. The angled progression together with the mentioned rotatability can correspondingly result in especially a lower area of the discharge channel describing a relatively large circle in relation to the floor of the dosing chamber during a rotation by comparison to a small area or one that only rotates around its own (geometric) longitudinal axis further above. This angling obviously also results in a stirring effect with regard to the substance in the supply chamber. In addition, it can favorably contribute to covering and releasing the entire dosing chamber through twisting around the rotational axis.

The dosing chamber is preferably provided with an opening that can be closed by a plug on its side lying opposite the discharge channel or on a side upstream in the direction of flow during substance removal. This plug can be used in particular to release a discharge air flow. When the plug has been removed from the opening, the discharge air flow can pass through.

In another detail, the dosing chamber can to this end preferably be lifted off of the plug. On the one hand, the plug can be movable relative to a fixed dosing chamber for this purpose. Since the dosing chamber is part of the supply chamber, it can on the other hand and preferably also be provided that the dosing chamber along with the storage chamber otherwise be movable in such a way as to yield the desired lifting from the plug. In a preferred embodiment, this corresponds to a movement by the dosing chamber and/or storage chamber in a vertical direction or in the alignment of the rotational axis of the discharge channel. In another preferred embodiment, the supply chamber along with the discharge channel can be moved toward a mouthpiece or away from the mouthpiece. In particular in conjunction with the discussed plug, the movement can release the bottom side of the dosing chamber, so that air aspirated by a user hits the floor of the dosing chamber, the floor of which is formed by the substance contained therein, as it were, and siphons in the contents of the dosing chamber in the discharge channel then aligned toward the dosing chamber. The dosing chamber is lifted from the fixed plug as part of the supply chamber. Given an opposite movement, the dosing chamber is hereby closed from below through placement on the plug.

In particular, the dosing chamber along with the discharge channel and/or only the floor of the supply chamber can thus be moved in the manner mentioned.

The discharge channel can be designed in particular as a suction channel. The aspiration of air by a user initially lifts the dosing chamber off of the plug (or vice versa) with the dosing chamber filled. This opens a flow path through the dosing chamber and into the discharge channel, and from there through the mouthpiece into the mouth of a user.

Removing the dosing chamber from the plug or pulling the plug out of a respective floor area of the dosing chamber might require the deliberate application of a force. As a result, the user is forced to exceed a specific negative pressure threshold during aspiration. As soon as the plug has been lifted, the air that then flows through inevitably results in a desired quick and complete evacuation of the dosing chamber through the discharge channel.

With respect to a sequence while a user performs an inhalation, the discharge channel, in particular in terms of its foot and further in particular in terms of the free flow cross section given in the foot, does not overlap the dosing chamber in an initial position in which the closing cap is still completely applied. While removing, in particular unscrewing, the closing cap, the discharge channel is rather first moved, in particular turned, so as to overlap the dosing chamber as required for inhalation purposes. The discharge channel here preferably rotates around a relevant rotational axis, which measures less than 360°. For example, it ranges between 270° and 330°, further preferably lies at 300°. This inevitably given rotation while moving the inhalator into an inhalation ready position necessarily ensures that the substance in the supply chamber will be influenced by the turning discharge channel before a respective inhalation. Possible bridges or the like in the substance caused by adhesion can be broken up. In addition, this rotation can be used to scoop-fill the dosing chamber, in particular by means of the foot of the discharge channel.

BRIEF DESCRIPTION OF THE DRAWINGS

The invention will further be explained below based on the drawing, which only presents an exemplary embodiment. Shown here on:

FIG. 9 is an outer view of the mouthpiece with rear part;

FIG. 10 is a view of the inhalator from above with closing cap removed;

DESCRIPTION OF THE EMBODIMENTS

Illustrated and described is an inhalator 1 for dispensing a powdery substance. In particular, the powdery substance is a pharmaceutical substance. The powder can contain an active agent, which can be removed from the inhalator by the user through inhalation.

Figure 1:
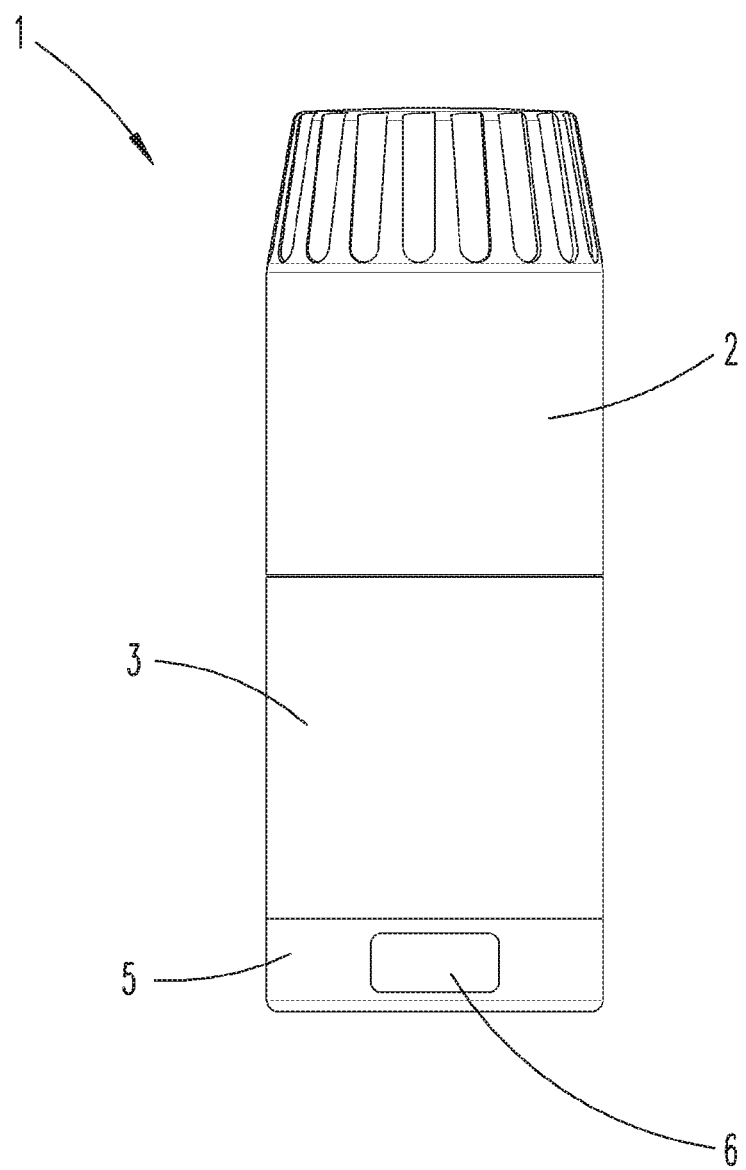
FIG. 1 is an outer view of the inhalator on the side having a counter display.

Visible in the view on FIG. 1 is an upper closing cap 2, and below that a rear part 3, which as yet to be explained below can be designed integrally with a mouthpiece 4. There is also a floor part 5 having a window 6 in the view on FIG. 1. A counting ring 7 of a counter preferably provided in the floor part can be visible through the window 6.

As evident, the inhalator 1 has an essentially cylindrical shape. In the exemplary embodiment and preferably, an upper part of the closing cap 2 is shaped so as to conically taper toward the respective end.

Figure 2:
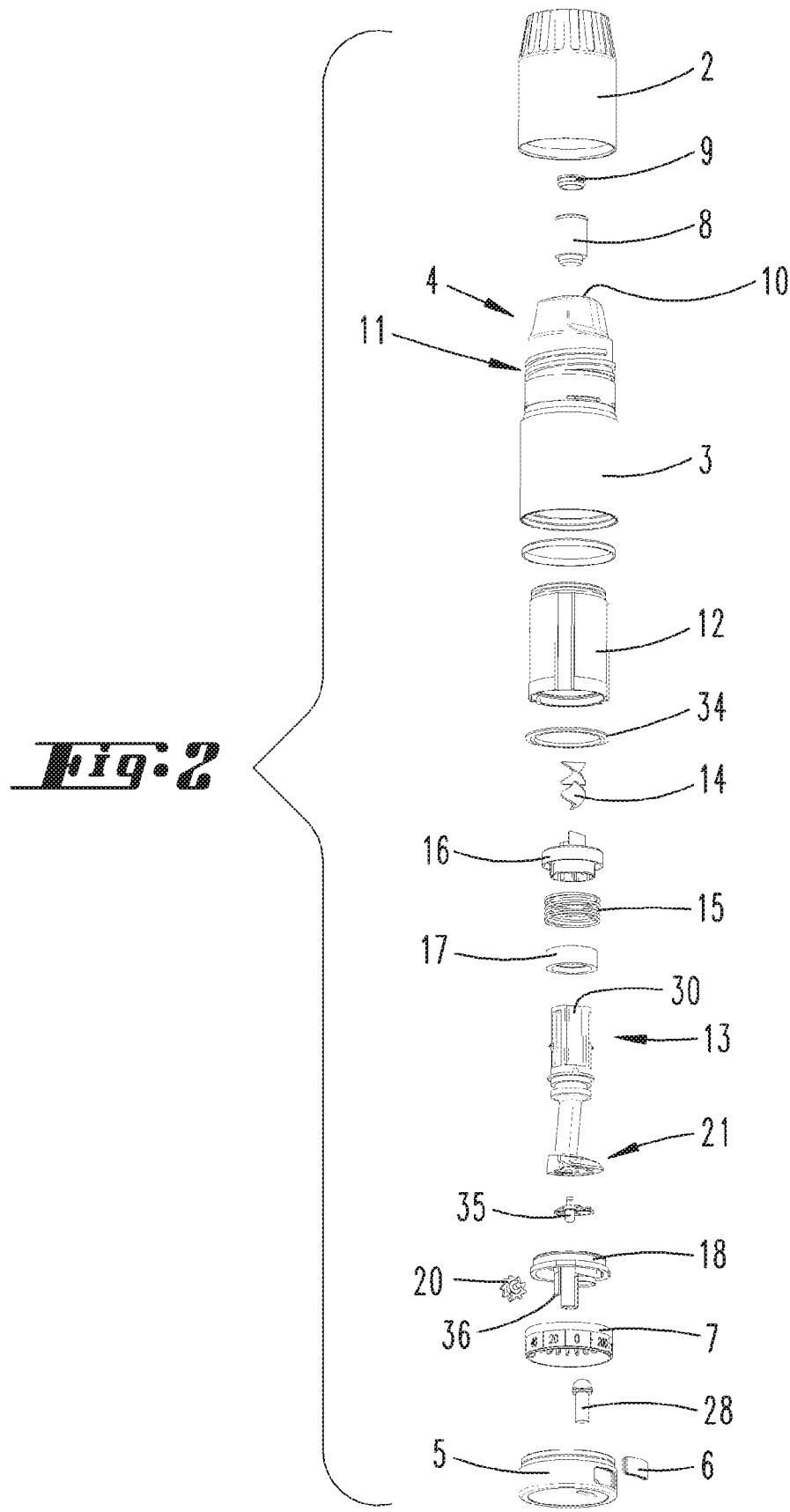
FIG. 2 is an exploded view of the inhalator.
Figure 3:
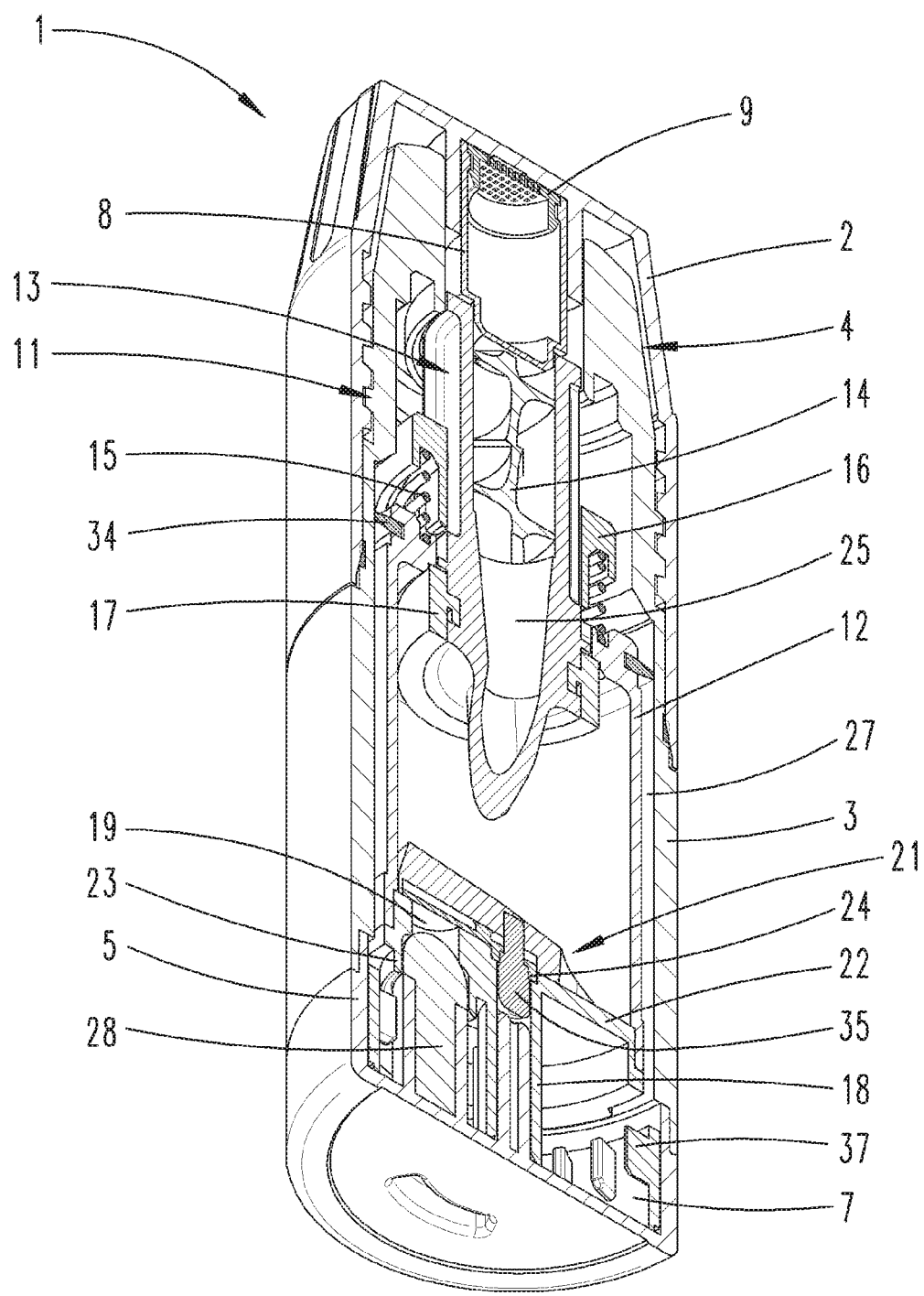
FIG. 3 is a perspective, longitudinal section through the inhalator.

The parts of the inhalator 1 are further evident from the exploded view on FIG. 2. A reservoir 8 can be arranged inside of the closing cap 2. The reservoir 8 can contain a dehumidifying means. The reservoir can be fastened, for example latched, inside of the cap 2 by a connecting part 9.

In the assembled state, the cap 2 flashes the rear part 3, which in the exemplary embodiment is integral in design with a mouthpiece 4.

Below the orifice section 10 usable by the user, the mouthpiece 4 or rear part 3 has a male thread 11 that can interact with a female thread in the closing cap 2. In the process of unscrewing, one or more catch elements 29 on the closing cap 2 can interact with corresponding catch elements 30 on a discharge channel 13, so that the discharge channel 13 rotates while unscrewing the closing cap 2.

The supply chamber 12 can extend inside of the rear part 3, preferably be accommodated as a separate chamber through which the discharge channel 13 penetrates. A turbulence means 14 can be arranged in the discharge channel 13, preferably allocated to the mouthpiece 4. The supply chamber 12 can be supported against a thrust bearing 16 by means of a spring 15. With the cap in place, the thrust bearing 16 can be pressurized by an entraining element 29, for example, so that the spring 15 acts on the supply chamber 12. The thrust bearing 16 can be guided along the discharge channel 13 so as to be axially displaceable, and if necessary also prevented from rotating. The discharge channel 13 can in any event be arranged in the supply chamber 12 so that it can rotate relative to the supply chamber 12.

A supply chamber floor part 18 can further be provided, in which the dosing chamber 19 can also be formed. The counting ring 7 and a driving wheel 20 acting on the latter can be arranged below the supply chamber floor part 18.

A plug 28 can be mounted in the floor part 5, so as to close or release the dosing chamber 19.

Figure 4:
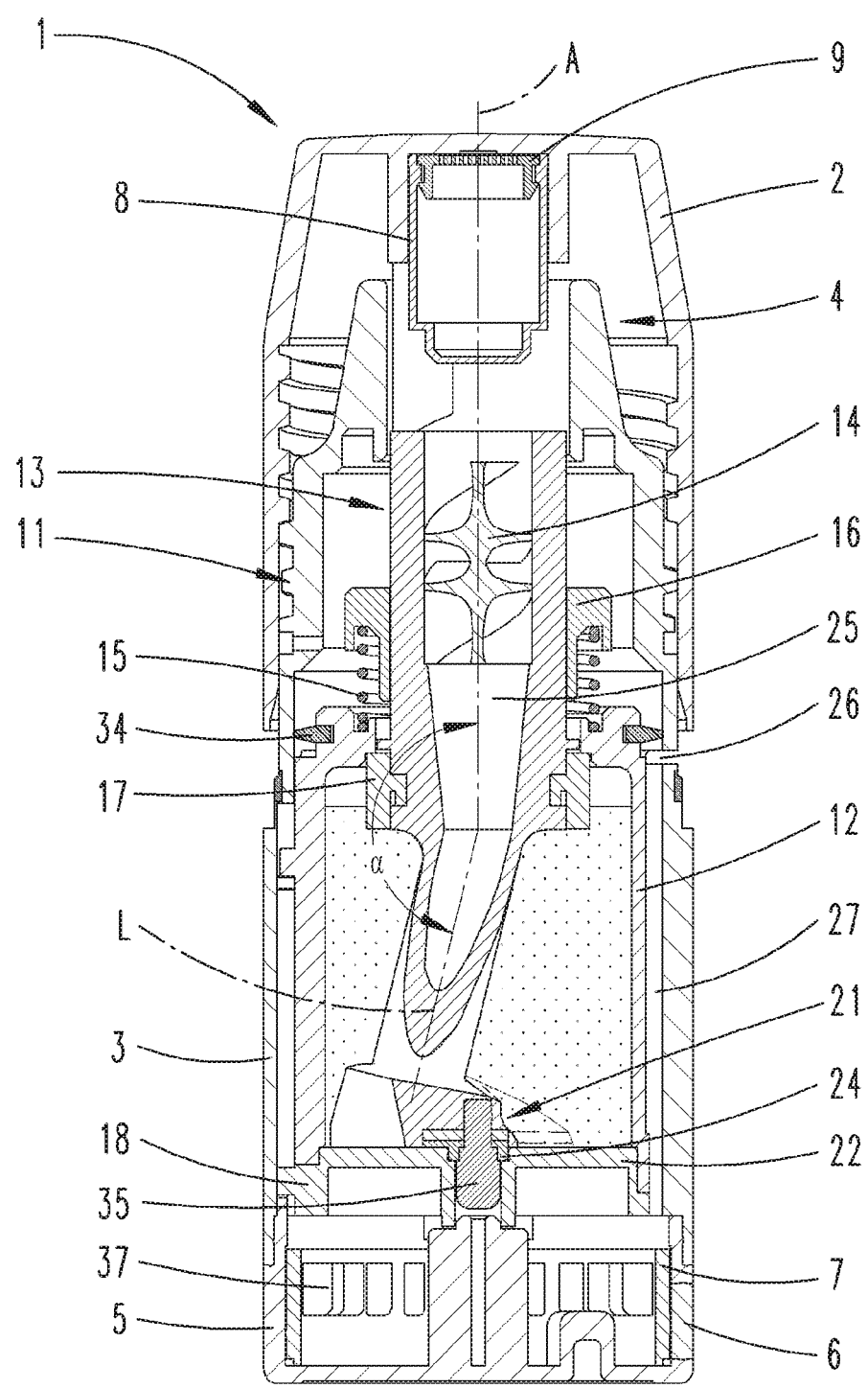
FIG. 4 is a longitudinal section through the inhalator while unscrewing the covering cap.
Figure 5:
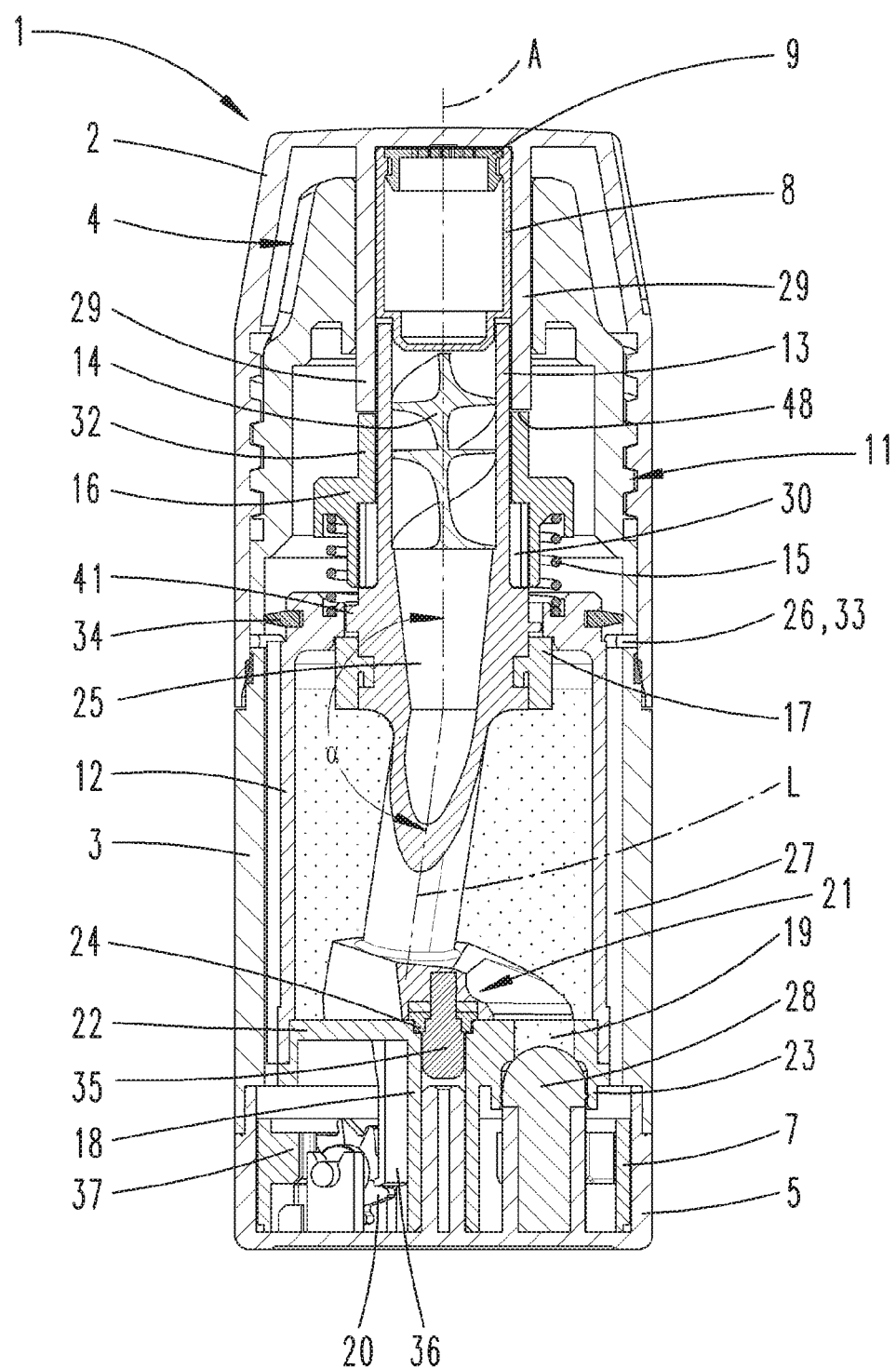
FIG. 5 is another longitudinal section through the inhalator with filled dosing chamber.
Figure 6:
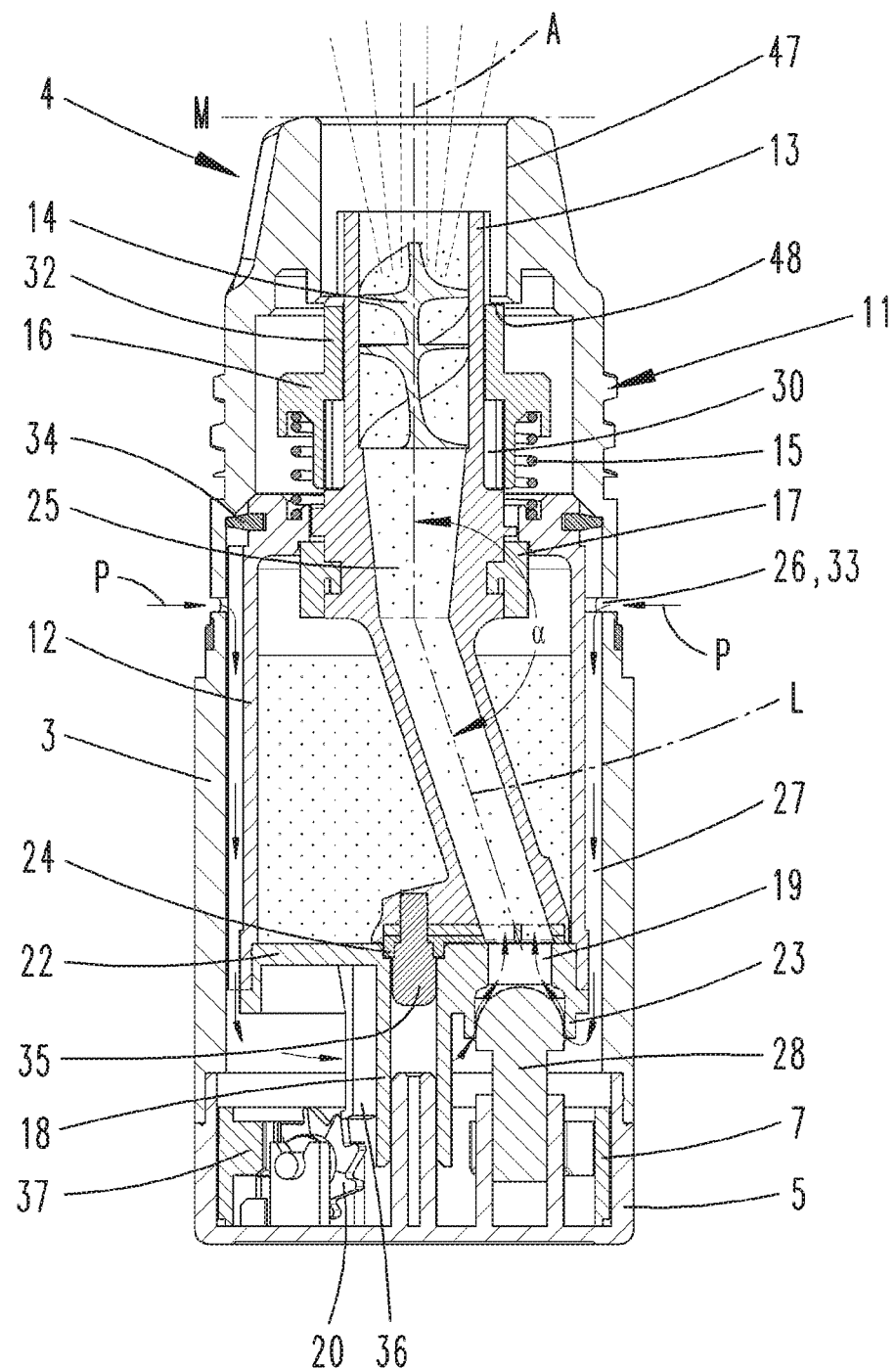
FIG. 6 is a longitudinal section according to FIG. 5, with the discharge channel moved over the dosing chamber and the dosing chamber lifted off of the plug.

As also evident from a comparison of FIGS. 4 to 6, for example, the discharge channel 13 is arranged in the inhalator 1 so that it can rotate around a rotational axis A. Preferably and in the exemplary embodiment, the rotational axis A coincides with a geometric axis of the inhalator 1 with respect to its cylindrical design.

Because the discharge channel 13 can be moved around the rotational axis A, the dosing chamber 19 can be filled while the discharge channel 13 rotates.

Preferably and in the exemplary embodiment, the discharge channel 13 has a foot 21. As the discharge channel 13 rotates around the rotational axis A, the foot 21 brushes over the supply chamber floor with an alternating covering that overall corresponds to a circular ring surface. In particular, a further detail of the foot is visible on FIGS. 7 and 8. The foot has a shape 31 that deviates from a circle (as viewed in the direction of the rotational axis A) in relation to the supply chamber floor 22. During a rotation, a respective part of the supply chamber floor can be exposed, while another is covered by the foot 21.

The dosing chamber 19 is formed in the supply chamber floor 22. In the exemplary embodiment and preferably, it is a chamber that extends downwardly proceeding from a surface of the supply chamber floor 22. A continuous, for example cylindrical, chamber wall 23 can be formed.

The dosing chamber 19 is preferably designed as a free passage opening. Depending on a specific rotational position of the discharge channel 13, it can be covered at the top by the discharge channel 13 or, if designed that way, by its foot 21. It can be closed by the plug 28 at the bottom.

The plug 28 can be removed from the dosing chamber in order to empty the dosing chamber 19.

The plug 29 preferably consists of a soft, for example elastomeric part. It can also be a rubber material. A thermoplastic elastomer can also be involved.

Alternatively, the chamber wall 23 can also consist of an elastic material, and the plug 20 of a hard material, such as hard plastic.

The plug 20 is preferably set up to interact with the chamber wall 23 in such a way that a specific threshold force must be overcome to pull the plug 20 out of the dosing chamber 19 so as to open the dosing chamber 19.

The threshold force is adjusted to the negative pressure that can be generated by a human user while performing an inhaling process.

The discharge channel 13 can be mounted below via a bearing protrusion 24 provided in the area of the supply chamber 12. The bearing projection 23 can be accommodated in a corresponding bearing recess of the supply chamber floor part 22, preferably centrally relative to the rotational axis A. As evident, a top section thereof projects at the top into a lower area of the discharge channel 13 or, in particular in the exemplary embodiment, into the foot 21. At a certain radius to a rotational axis of the bearing projection 24, an area can arise in the area of the bearing projection 24 in which the supply chamber floor 22 is constantly covered, regardless of the rotational position of the discharge channel 13.

Figure 7:
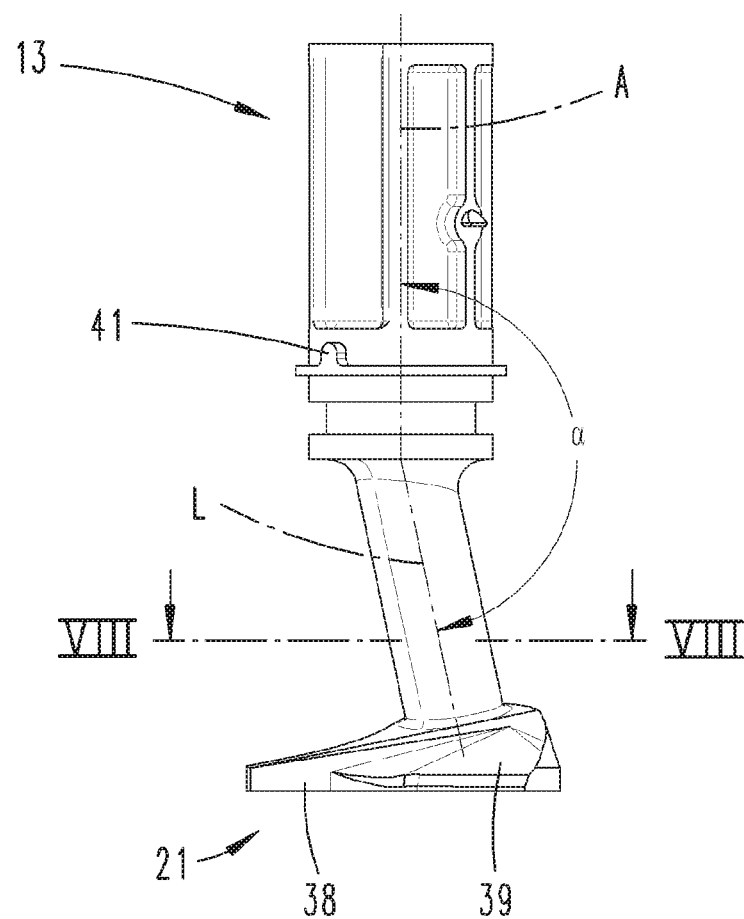
FIG. 7 is an outer view of the discharge channel.
Figure 8:
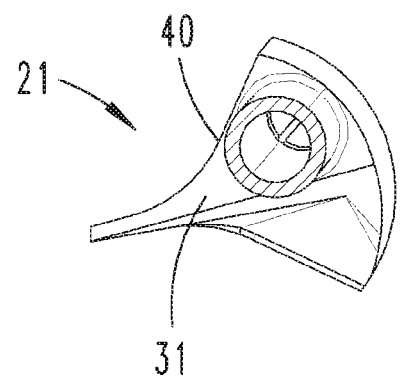
FIG. 8 is a cross section through the object according to FIG. 7, cut along the VIII-VIII line.
Figure 11:
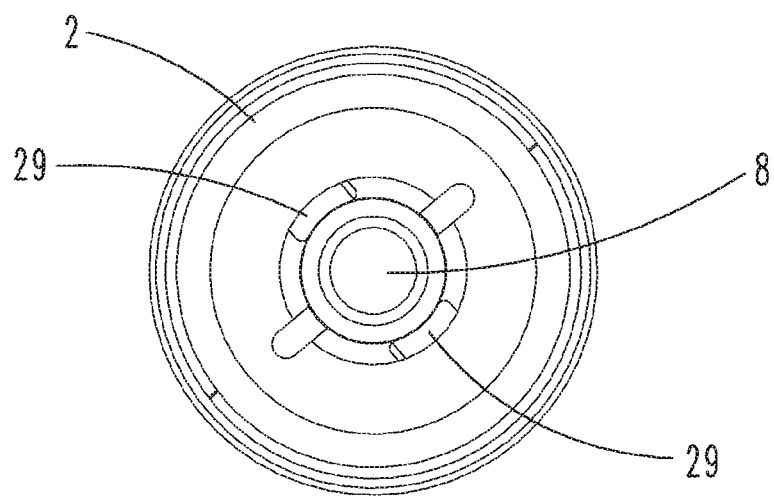
FIG. 11 is a lower side of the closing cap.

As further also evident from FIGS. 7 and 8, the peripheral edges of the foot 21 are shaped like a scoop. As the discharge channel 13 or foot 21 rotates, a scooping of the dosing chamber 19 can take place, as it were, so as to fill it.

Further preferably and in the exemplary embodiment, the discharge channel 13 is provided with a kinked progression. While an essentially rotationally symmetrical extension to the rotational axis A is formed in its upper area allocated to an upper end of the supply chamber 12 and extending until into the mouthpiece 4, a kink is provided in the lower area, in the exemplary embodiment and preferably solely in the supply chamber 12. A longitudinal axis L of the kinked area preferably includes an obtuse angle $\alpha$ of 100°-175° with the rotational axis A. In the exemplary embodiment and preferably, it measures 155°-175°, and further preferably approx. 168°. The discharge channel further preferably consists of a few, further preferably only two, sections that each run along a straight line.

The discharge channel 13 has an inner cavity 25, through which substance-laden suction air is transported from the supply chamber floor to the mouthpiece 4 during an inhalation.

As evident and preferred, this cavity 25 in the area of the longitudinal axis L is formed with a smaller diameter, and then expands into a larger diameter.

The turbulence element 14 is arranged in the area of the larger diameter and upstream from the mouthpiece 4 in the outflow direction. Preferably with regard to the rotational axis A in the area of the gasket 17, one or more through openings 26 are formed in the rear part 3. With the closing cap 2 unscrewed, the user can aspirate air from outside through these through openings 26, which then flows through an air channel 27 below the supply chamber floor 22, for example one designed as an annular chamber, and further through the dosing chamber 19, expelling the substance then contained therein, and loaded with the substance into the cavity 25 of the discharge channel 13.

Figure 12:
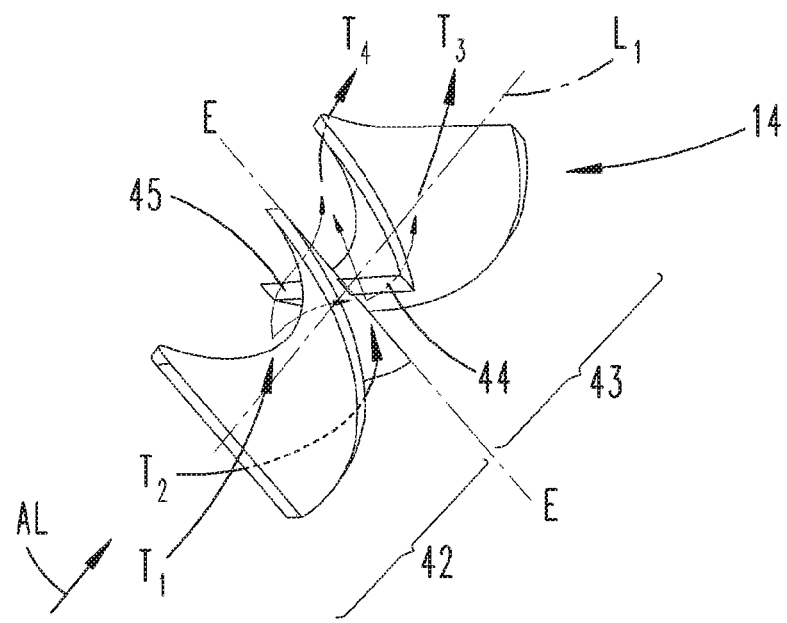
FIG. 12 is a separate, perspective illustration of the turbulence means.

The turbulence means 14 is shown in further detail on FIG. 12. It consists of partial areas 42 and 43 arranged one after the other in an axial direction. Each partial area 42 and 43 preferably in itself corresponds to a conventional helical turbulence device. Between the partial areas 42 and 43, however, these partial areas, in a plane E-E running perpendicular to a longitudinal axis $L_1$ of the turbulence means 14, are separated, as it were, out of a continuous helical part that theoretically contains these partial areas and then angularly displaced, specifically by a rotational angle of 90°, and then brought together again. For the suction air AL loaded with substance and flowing into the partial 42 that is first, lowermost or first in the flowing direction, the respective first partial flows $T_1$ and $T_2$ thus impact respective dividing edges 44, 45 of the second partial area 43, which divide the first partial flows $T_1$, $T_2$ into second partial flows $T_3$, $T_4$, wherein these second partial flows $T_3$, $T_4$ are again based upon bringing together portions of the first partial flows $T_1$, $T_2$. The turbulence means 14 is preferably also designed in such a way as to deflect each partial flow $T_1$ to $T_4$ so that it completes roughly a quarter rotation or more around the longitudinal axis $L_1$.

As also evident in particular from a comparison of FIGS. 5 and 6, the discharge channel 13 is made to rotate in the process of unscrewing by removing the entraining element 29 from the entraining formations 30, as long as the latter are not yet overlapping. This rotation can preferably measure up to 360° or slightly less, but at any rate preferably 300° or more. At the same time, removing the entraining elements 29 frees up space in the entraining formations 30 in a vertical direction for engaging areas 32 of the thrust bearing 16 that are preferably also guided in the entraining formations 30. The thrust bearing 16 moves upward, and with the closing cap removed closes the entraining formations 30.

In a state covered and closed by the closing cap 2, e.g., one corresponding to FIG. 1, the cavity 25 or a relevant food-side orifice of the discharge channel 13 does not overlap the dosing chamber 19. In this state, the dosing chamber 19 is preferably completely exposed toward the interior of the supply chamber 12, see FIG. 5. As a result, the dosing chamber 19 can in particular have already been filled to a certain extent from the supply chamber 12 given a preceding twisting of the discharge channel 13 also initiated while screwing on the closing cap, or directly out of the supply chamber 12 through exposure to gravity.

While the thrust bearing 16 is driven up after unscrewing is complete, as evident from FIG. 6, the dosing chamber 19 is still in the closed position shown on FIG. 5, and the supply chamber 12 is also still in the position shown on FIG. 5. If a user then applies a negative suction pressure to the mouthpiece 4, the discharge channel 13 along with the dosing chamber 12 is lifted into the position depicted on FIG. 6. As shown by the arrows P, air can be siphoned through openings 33 in the rear part 3 into the gap between the dosing chamber 12 and rear part 3, and enter into the dosing chamber 19 from below. The dosing chamber 19 is thereby evacuated into the discharge channel 13, and the content of the dosing chamber is sucked in by the user, if necessary after passing through the turbulence means 14.

The discharge channel 13 can thus be moved relative to the mouthpiece 4 out of a first position, in which the end of the discharge channel 13 of an orifice plane M of the mouthpiece 4 is closer, see FIG. 6, into a second position, see FIG. 5, in which the end of the discharge channel of the orifice plane is more remote, and vice versa. Preferably and in the exemplary embodiment, the discharge channel 12 can be moved together with the supply chamber 12 in this regard.

At any rate, the entraining elements 29 on the closing cap 2 also described here yield one or several influencing sections in this regard, so as to cause the discharge channel 13 and/or supply chamber 12 to move between the first and second positions.

With the closing cap 2 screwed on, e.g., see FIGS. 4 and 5, the thrust bearing 16 and spring 15 ensure that the dosing chamber 19 has again moved over the plug 28, and is thus closed from below. The thrust bearing 16 presses down the dosing chamber 19—and thereby preferably the discharge channel 13 at the same time.

The upper side of the dosing chamber 12 is further sealed against an interior surface of the rear part 3 with a continuous gasket 34. While screwing and unscrewing the cap 2, this gasket moves accordingly in a vertical direction along an interior surface of the rear part 3.

On the floor side of the discharge chamber 12, the discharge channel 13 is rotatably mounted in the supply chamber floor 22 by means of a bearing pin 35. Preferably and in the exemplary embodiment, the configuration is such that a rotational axis passing through the bearing pin 35 penetrates through a portion of the free supply chamber in a vertical elongation due to the mentioned kinking and formation of the foot.

Once inhalation is complete and the user has replaced the closing cap 2, the entraining elements 29, for example which can be designed as opposing rib elements that are bent in the circumferential direction, impact an interior surface 46, see FIG. 10, which is designed to circularly run on the upper, extended area of the discharge channel 13 inside a preferably cylindrical interior surface 47 of the mouthpiece 4. In part, preferably at two opposing areas, this surface 46 is formed by the end face 48 of the thrust bearing 16 with the inhalator in this state. In another detail, the end faces 48 can be provided at engagement areas 32 of the thrust bearing 16 that run parallel to the rotational axis A and protrude upwardly toward the orifice.

During placement, the thread of the closing cap 2 can be made to engage the male thread 11 if the entraining elements 29 have previously struck the mentioned end faces 48 of the thrust bearing 16 in a corresponding angular alignment, and have downwardly pressed this thrust bearing 16 by a first amount against the force of the spring 15.

It is further preferred that the force set for the spring 15 be stronger than a displacement resistance offered by the combination of the discharge channel 13 and supply chamber 12 against a downward displacement, i.e., from the position on FIG. 6 into the position on FIG. 5. As a consequence, downwardly pressing the thrust bearing 16 initially yields a downward displacement of the discharge chamber 13 along with the supply chamber 12 while correspondingly pressing the closing cap 2 toward the rotational axis A, even if the entraining elements 29 are already aligned relative to the end faces 48. As a result, the discharge channel 13 can also be prevented from moving, in particular rotating, relative to the supply chamber 12 before the dosing chamber 19 has been closed once again on the floor side. Against further resistance while screwing on the closing cap 2, the entraining elements 29 then move deeper into the corresponding openings in the circular ring surface 46, and press the thrust bearing 16 into the position according to FIG. 4 while compressing the springs 15, in the completely screwed state of the closing cap 2. With the entraining elements 29 retracted, rotating the closing cap 2 simultaneously causes the discharge channel 13 to rotate relative to the supply chamber 12. It is here also preferred that it only be possible to retract the entraining elements 29 into the entraining formations 30 after a specific threaded engagement has been established. The closing cap 2 can then no longer be pulled off toward the top.

It is further preferred that the thread of the closing cap 2 and the male thread 11 on the housing of the inhalator only engage into each other with the closing cap 2 aligned at a specific rotational angle. As a consequence, a precisely defined twisting of the discharge channel 13 relative to the fixed supply chamber 12 is achieved by the time of the complete rotational closure of the closing cap 2, thus yielding the desired alignment of the discharge channel 13 relative to the dosing chamber 19 with the closing cap 2 screwed on completely.

An entrainer 36 is secured to the supply chamber floor part 18 further toward the lower side. This entrainer is part of the counter, and interacts with the driving wheel 20. The driving wheel 20 further interacts with a backflow preventer, which is not shown in detail.

When driving up the supply chamber 12 and in particular the supply chamber floor 22, the driving wheel 20 is entrained to an angular extent by the entrainer 36. The driving wheel 20 is preferably designed as a worm shaft, further preferably as a single-thread worm shaft, with a screw helix pitch adjusted to the spacing of entraining projections 37 on the counting ring 7. The entraining projections 37 are obviously directed inwardly in relation to the counting ring 7. An entraining projection allocated to the respective driving wheel 20 enters between the flanks of the screw helixes at roughly the height of a rotational axis of the driving wheel 20. Given a rotational displacement of the driving wheel 20, the engaged entraining projection is correspondingly displaced in the horizontal direction, i.e., transverse to the rotational axis A. As a result, the counting wheel 7 is correspondingly turned.

Each time the cap 2 is screwed shut, the counting wheel 7 is thus incrementally turned.

With respect to the configuration of the counter, reference is further also made to WO 2007/104698 A1, in particular to FIGS. 13 to 19 and the accompanying description, and also to the parallel U.S. Pat. No. 8,261,737 B2, in terms of the figures with the same numeration and the relevant description.

The function and configuration are the same, with the only difference being that, in the subject matter of the mentioned publications, counting takes place when pressing down to load the dosing chamber, and that the entrainer 36 overlaps the driving wheel 20 at rest, here with the cap 2 screwed on.

In an extension of the rotational axis, the inhalator 1 has a length overall that is adjusted to the width of a hand of a human user, for example, up to two or three times the width of the hand of a human user. As consequence, the inhalator in this extension can have a length of 7 to 20 cm, for example.

The diameter in the cylindrical area can measure 5 to 10 cm, for example.

With respect to FIGS. 7 and 8, the foot 21 has a relatively steep flank 38 radially inward, roughly overlapping vertically to the bearing pin 35, which transitions radially outside into a scoop surface 29. The flank 38 can include an acute angle of 0° to 30° with a vertical, while the scoop surface 39, if necessary also varyingly angled in relation to its radial extension, can include an angle with a vertical ranging from 20° to 40°. Regardless of the specifically selected angular alignment, it is always preferred that the flank 38 be steeper than the scoop surface 39. This configuration is obviously given on one side in the rotational direction, while only a continuous counter-flank 40 is formed on the opposite side. The counter-flank 40 preferably also has a steep design. It can also include an angle with a vertical corresponding to the rotational axis A of 0° to 30°.

A rotational stop is preferably also formed with regard to the discharge channel 13. To this end, a stop projection 41 can be formed on the discharge channel 13, and a corresponding counter-stop on the supply chamber 12, specifically a supply chamber cover through whose vertically continuous opening the discharge channel 13 passes. At any rate, no complete 360° rotation is thus enabled.

The above statements serve to explain the inventions encompassed by the application overall, which further develop the prior art at least through the following feature combinations, and even independently as well, specifically:

A hand operable inhalator 1, characterized in that the discharge channel 13 can be rotated around a rotational axis A, and that the dosing chamber (19) can be filled while rotating the discharge channel 13.

Inhalator 1, characterized in that the rotational axis A runs at least partially along a transport direction prescribed by the discharge channel 13 for the substance transported in the discharge channel.

Inhalator 1, characterized in that the dosing chamber 19 is eccentrically arranged relative to the rotational axis of the discharge channel 13.

Inhalator 1, characterized in that the dosing chamber 19 is separate from the discharge channel 13.

Inhalator 1, characterized in that the dosing chamber 19 is located on the floor side of the supply chamber 12.

Inhalator 1, characterized in that the discharge channel 13 has a foot, which as the discharge channel 13 rotates releases the dosing chamber 19 for filling purposes.

Inhalator 1, characterized in that a lower side of the discharge channel 13 runs in-plane with a floor 22 of the supply chamber outside of the dosing chamber 19.

Inhalator 1, characterized in that the discharge channel 13 has an angled progression relative to a flow path formed therein.

Inhalator 1, characterized in that the side of the dosing chamber 19 lying opposite the discharge channel 13 has an opening that can be closed by a plug 28.

Inhalator 1 according to one of the preceding claims, characterized in that the dosing chamber 19 can be lifted from the plug 28, wherein the dosing chamber 19 can preferably be moved together with the discharge channel 13.

| Reference List | |
|---|---|
| 1 | Inhalator |
| 2 | Closing cap |
| 3 | Rear part |
| 4 | Mouthpiece |
| 5 | Floor part |
| 6 | Window |
| 7 | Counting ring |
| 8 | Reservoir |
| 9 | Connecting part |
| 10 | Orifice section |
| 11 | Male thread |
| 12 | Supply chamber |
| 13 | Discharge channel |
| 14 | Turbulence means |
| 15 | Spring |
| 16 | Thrust bearing |
| 17 | Gasket |
| 18 | Supply chamber floor part |
| 19 | Dosing chamber |
| 20 | Driving wheel |
| 21 | Foot |
| 22 | Supply chamber floor |
| 23 | Chamber wall |
| 24 | Bearing projection |
| 25 | Cavity |
| 26 | Through opening |
| 27 | Air channel |
| 28 | Plug |
| 29 | Entraining element |
| 30 | Entraining formation |
| 31 | Formation |
| 32 | Engagement area |
| 33 | Opening |
| 34 | Gasket |
| 35 | Bearing pin |
| 36 | Entrainer |
| 37 | Entraining projection |
| 38 | Flank |
| 39 | Scoop surface |
| 40 | Counter flank |
| 41 | Stop projection |
| 42 | Partial area |
| 43 | Partial area |
| 44 | Dividing edge |
| 45 | Dividing edge |
| 46 | Interior surface/circular ring surface |
| 47 | Interior surface |
| 48 | End face |
| A | Rotational axis |
| AL | Suction air |
| α | Angle |
| E | Plane |
| L | Longitudinal axis |
| $L_1$ | Longitudinal axis |
| M | Orifice plane |
| P | Arrow |
| $T_1$ | Partial flow |
| $T_2$ | Partial flow |

-continued

Reference List

| | |
|---|---|
| T$_3$ | Partial flow |
| T$_4$ | Partial flow |
| V | Vertical |

The invention claimed is:

1. A hand operable inhalator (1) for dispensing a powdery substance, comprising: a supply chamber, a discharge channel (13) and a dosing chamber (19), wherein the discharge channel protrudes into the supply chamber (12), and the dosing chamber (19) and discharge channel (13) can be moved relative to each other, wherein the discharge channel (13) can be rotated around a rotational axis (A), and wherein the dosing chamber (19) can be filled while the discharge channel (13) rotates, wherein a side of the dosing chamber (19) lying opposite the discharge channel (13) has an opening that can be closed by a plug (28), wherein the dosing chamber (19) can be lifted from the plug (28), and wherein the dosing chamber (19) can be moved together with the discharge channel (13).

2. The inhalator according to claim 1, wherein the rotational axis (A) runs at least partially along a transport direction prescribed by the discharge channel (13) for the substance transported in the discharge channel.

3. The inhalator according to claim 1, wherein the dosing chamber (19) is eccentrically arranged relative to the rotational axis of the discharge channel (13).

4. The inhalator according to claim 1, wherein the dosing chamber (19) is separate from the discharge channel (13).

5. The inhalator according to claim 1, wherein the dosing chamber (19) is located on the a floor side of the supply chamber (12).

6. The inhalator according to claim 1, wherein the discharge channel (13) has a foot, which, as the discharge channel (13) rotates, releases the dosing chamber (19) for filling purposes.

7. The inhalator according to claim 1, wherein a lower side of the discharge channel (13) runs in-plane with a floor (22) of the supply chamber.

8. The inhalator according to claim 1, wherein the discharge channel (13) has an angled progression relative to a flow path formed therein.

9. The inhalator according to claim 1, further comprising a mouthpiece, wherein the supply chamber (12) together with the discharge channel (13) can be moved relative to the mouthpiece (4) so as to displace the dosing chamber (19) from a closed into an open state and vice versa.

10. The inhalator according to claim 1, wherein the discharge channel (13) incorporates a turbulence means (14), which has a helically running wall and is configured to carry a flow while discharging air provided with the substance, wherein the helically running wall divides the air flowing through the discharge channel into partial flows (T$_1$, T$_2$) guided thereafter in an entry area, and the first partial flows (T$_1$, T$_2$) ensuing in a direction of flow in an interruption area are divided into second partial flows (T$_3$, T$_4$) that are thereafter guided adjacent to one another, wherein at least one of the second partial flows (T$_3$, T$_4$) is based on a convergence of portions of both first partial flows (T$_1$, T$_2$).

11. The inhalator according to claim 1, further comprising a mouthpiece that has an orifice plane, and a closing cap (2) configured for flashing the mouthpiece (4) and one end of the discharge channel (13) allocated to the mouthpiece (4), wherein the discharge channel (13) can be moved relative to the mouthpiece (4) from a first position in which the end of the discharge channel (13) is closer to the orifice plane, into a second position in which the end of the discharge channel (13) is further away from the orifice plane, and vice versa, and wherein an influencing section is provided on the closing cap (2) so as to cause the discharge channel (13) or supply chamber (12) to move from the first position into the second position.

* * * * *